US009568177B2

(12) United States Patent
Ferguson (10) Patent No.: US 9,568,177 B2
(45) Date of Patent: Feb. 14, 2017

(54) MEDICAL HEADLAMP ASSEMBLY HAVING INTERCHANGEABLE HEADLAMP TYPES WITH KEY RESISTORS

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 43 days.

(21) Appl. No.: 14/750,754

(22) Filed: Jun. 25, 2015

(65) Prior Publication Data

US 2015/0289943 A1 Oct. 15, 2015

Related U.S. Application Data

(63) Continuation-in-part of application No. 14/162,244, filed on Jan. 23, 2014, now Pat. No. 9,091,428, which
(Continued)

(51) Int. Cl.
*A61B 19/00* (2006.01)
*F21V 23/02* (2006.01)
(Continued)

(52) U.S. Cl.
CPC .............. *F21V 23/02* (2013.01); *A61B 1/0692* (2013.01); *A61B 90/30* (2016.02); *F21L 4/00* (2013.01); *F21L 15/14* (2013.01); *F21V 21/084* (2013.01); *F21V 33/0068* (2013.01); *H05B 33/0815* (2013.01); *H05B 33/0842* (2013.01); *A61B 2090/309* (2016.02); *A61B 2090/502* (2016.02);
(Continued)

(58) Field of Classification Search
CPC . F21V 33/0068; F21V 21/048; A61B 16/5202
See application file for complete search history.

(56) References Cited

U.S. PATENT DOCUMENTS 4,296,402 A * 10/1981 Szczepanski ......... B60R 25/045
123/179.3
7,210,810 B1 5/2007 Iversen et al.
(Continued)

FOREIGN PATENT DOCUMENTS

EP 2479489 A2 7/2012
KR 1020110095674 A1 8/2011
(Continued)

*Primary Examiner* — David V Bruce
(74) *Attorney, Agent, or Firm* — Timothy E. Siegel Patent Law, PLLC; Timothy E. Siegel (57) ABSTRACT

A medical headlamp assembly, having a headband subassembly, including an electrical network, including a battery and an electrical jack, and a headlamp mount. Also, an electrical headlamp subassembly, has a mounting element matingly and removably engaged to the headlamp mount, and an electrical plug, matingly and removably engaged to the jack and an electrical headlamp, electrically connected to the plug. Further, the headband subassembly produces an electrical input for the headlamp subassembly and the headband subassembly includes a key resistor, the resistance value of which sets a characteristic of the electrical input.

8 Claims, 10 Drawing Sheets

Related U.S. Application Data is a continuation-in-part of application No. 14/057,351, filed on Oct. 18, 2013, now Pat. No. 9,351,799.

(60) Provisional application No. 61/822,493, filed on May 13, 2013.

(51) Int. Cl.
| | |
|---|---|
| *F21V 33/00* | (2006.01) |
| *F21V 21/084* | (2006.01) |
| *F21L 4/00* | (2006.01) |
| *A61B 1/06* | (2006.01) |
| *F21V 21/08* | (2006.01) |
| *H05B 33/08* | (2006.01) |
| *F21W 131/20* | (2006.01) |
| *F21Y 101/00* | (2016.01) |

(52) U.S. Cl.
CPC ....... *F21W 2131/20* (2013.01); *F21Y 2101/00* (2013.01); *Y10T 29/49117* (2015.01)

(56) References Cited

U.S. PATENT DOCUMENTS

| | | |
|---|---|---|
| 2005/0117327 A1 | 6/2005 | Gupta |
| 2006/0285316 A1 | 12/2006 | Tufenkjian et al. |
| 2011/0026258 A1 | 2/2011 | Chang |
| 2012/0120635 A1 | 5/2012 | Strong et al. |

FOREIGN PATENT DOCUMENTS

| | | |
|---|---|---|
| WO | 2009063224 A2 | 5/2009 |
| WO | 2010144426 A1 | 12/2010 |

* cited by examiner

MEDICAL HEADLAMP ASSEMBLY HAVING INTERCHANGEABLE HEADLAMP TYPES WITH KEY RESISTORS

RELATED APPLICATIONS

This application is a continuation-in-part of application Ser. No. 14/162,244 filed on Jan. 23, 2014 which is itself a continuation-in-part of application Ser. No. 14/057,351, filed on Oct. 18, 2013, which are incorporated herein by reference as if fully set forth herein, and which, in turn, claims priority from provisional application Ser. No. 61/822,493, filed May 13, 2013, which is also incorporated by reference as if fully set forth herein.

BACKGROUND

Medical headlamp providers have attempted to make a single design that serves a variety of purposes, and in so doing have diminished the capability of such a design to perform any single specialized purpose. For example, many designs feature an adjustable iris, to permit a user to set the beam width of the light produced. Unfortunately, such an iris blocks a good deal of the light, thereby requiring a brighter light source, needing more power.

It is an undesirable expense, however, to purchase a separate head lamp assembly for each purpose that a physicians' office or hospital department may require. It would be desirable to find a way to eliminate at least part of this expense.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a medical headlamp assembly, having a headband subassembly, including an electrical network, including a battery and an electrical jack, and a headlamp mount. Also, an electrical headlamp subassembly, has a mounting element matingly and removably engaged to the headlamp mount, and an electrical plug, matingly and removably engaged to the jack and an electrical headlamp, electrically connected to the plug. Further, the headband subassembly produces an electrical input for the headlamp subassembly and the headband subassembly includes a key resistor, the resistance value of which sets a characteristic of the electrical input.

In a second separate aspect, the present invention may take the form of a method of switching out a medical headlamp that utilizes a medical headlamp assembly having a headband assembly, including a mounting element, an electrical jack and a power supply assembly electrically connected to the electrical jack. Also, a first headlamp assembly is removably engaged to the mounting element and includes a conductor terminating in a plug that is plugged into the jack, and a first key resistor for setting an electrical input. Also, a second headlamp assembly is removeably engageable to the mounting element and includes a conductor terminating in a plug that is engageable to the jack and a second key resistor for setting the electrical input differently than for the first headlamp. In the method, the first headlamp assembly is removed from the mounting element, the first headlamp plug is unplugged from the jack, the second headlamp is engaged on the mounting element, and the second headlamp plug is plugged into the jack.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Referring to FIGS. 1-6, in a first preferred embodiment a medical headlamp assembly 10 includes a headband 12, supporting a mounting column 14. A low intensity headlamp assembly 16 includes a low intensity headlamp 18, a linkage 20, a slider 22. Also included is an electrical conductor 26 terminating in a four pole audio plug 28, which plugs into a four pole audio jack 30.

Figure 1:
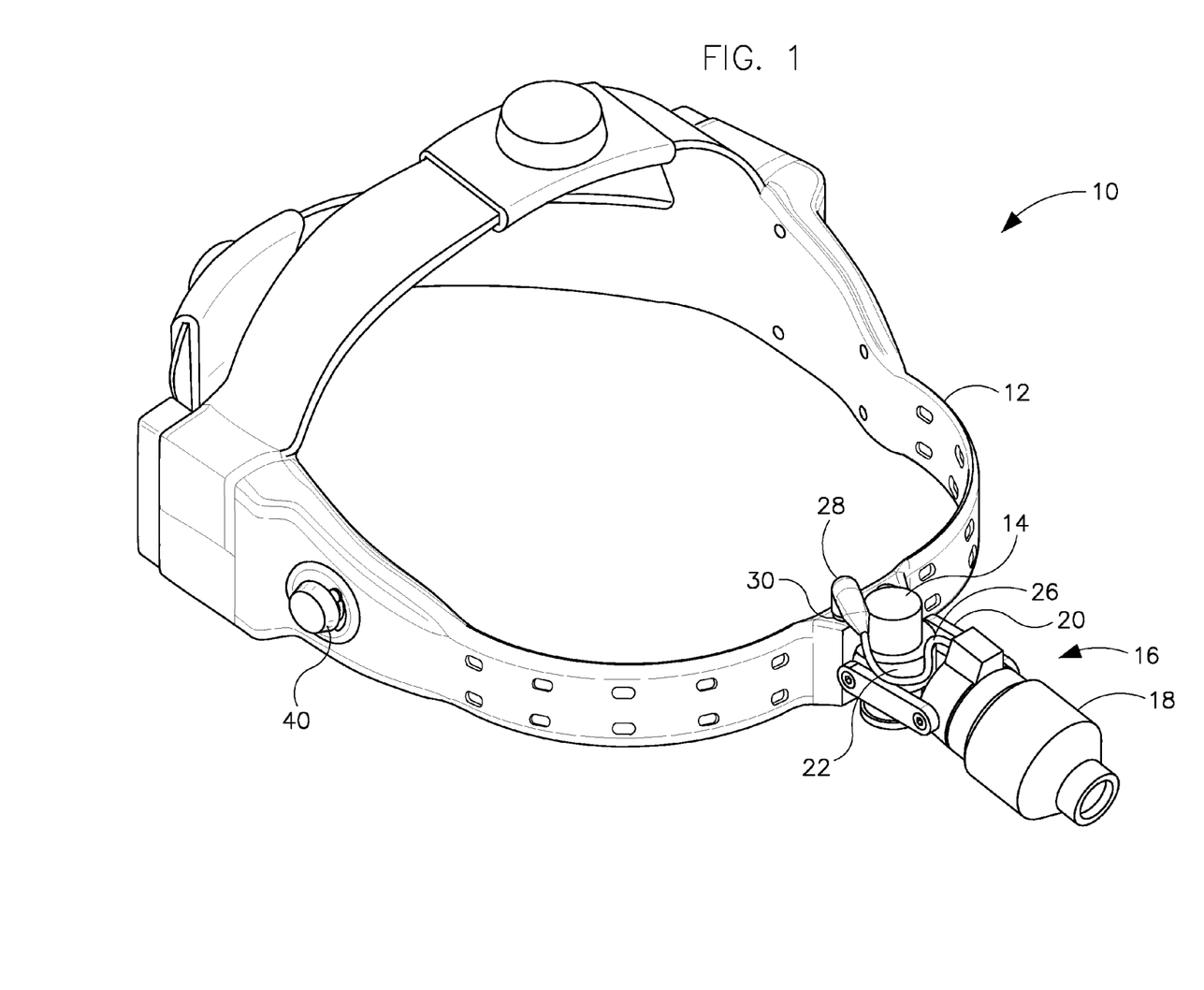
FIG. 1 shows an isometric view of a medical headlamp assembly, having an attached medical headlamp of a first type.
Figure 2:
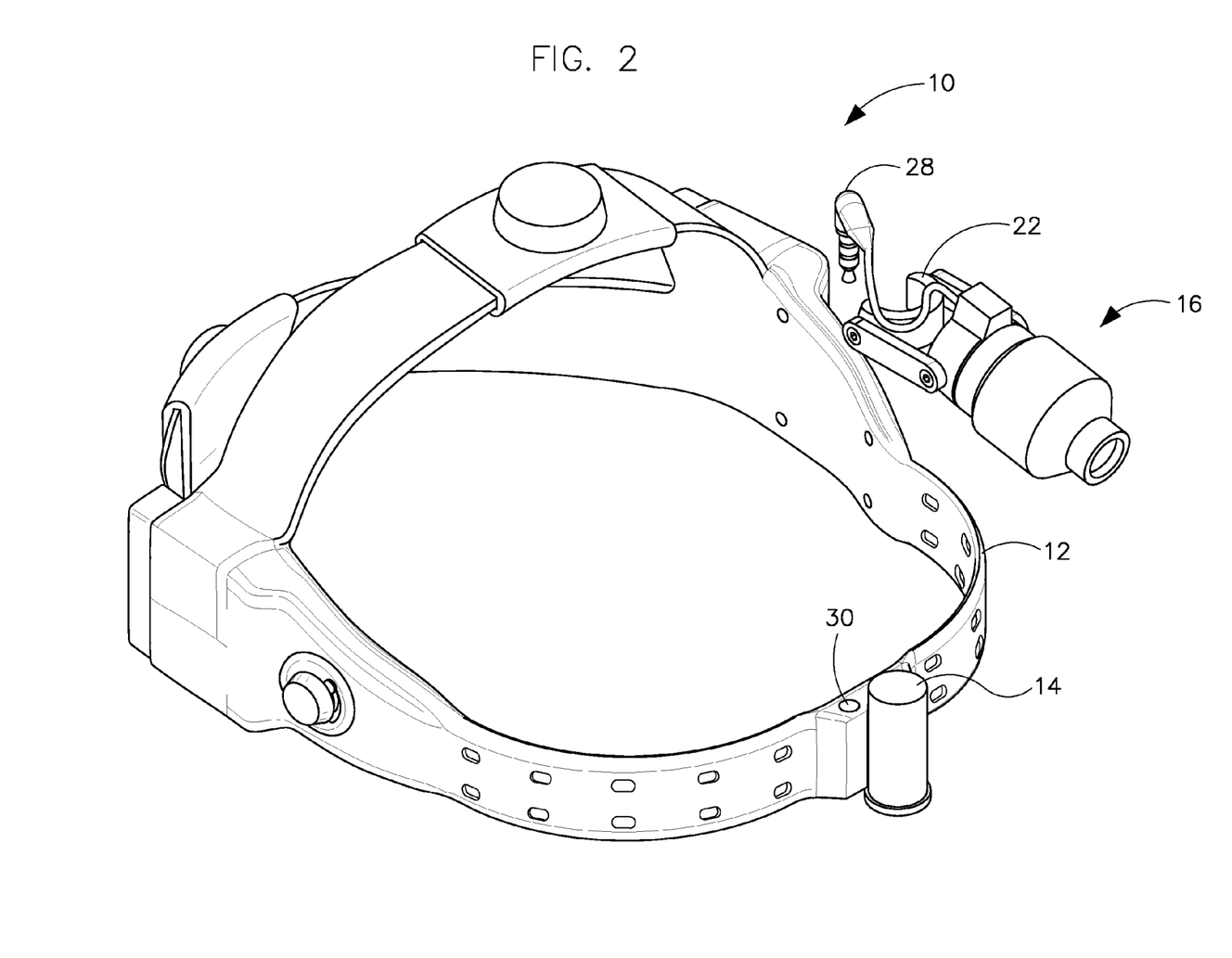
FIG. 2 shows an isometric view of a medical headlamp assembly, having a detached medical headlamp of the first type.
Figure 3:
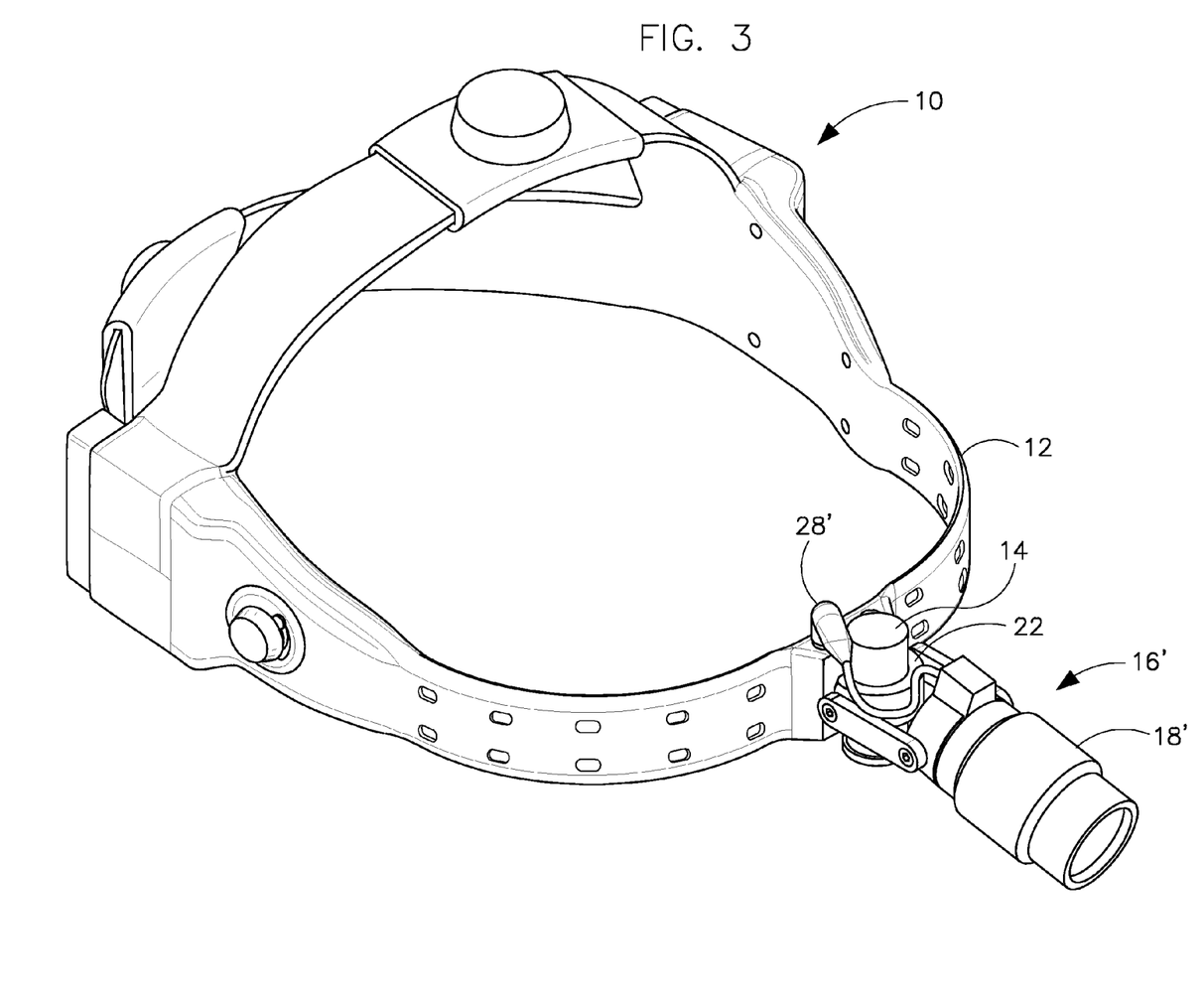
FIG. 3 shows an isometric view of a medical headlamp assembly, having an attached medical headlamp of a second type.
Figure 4:
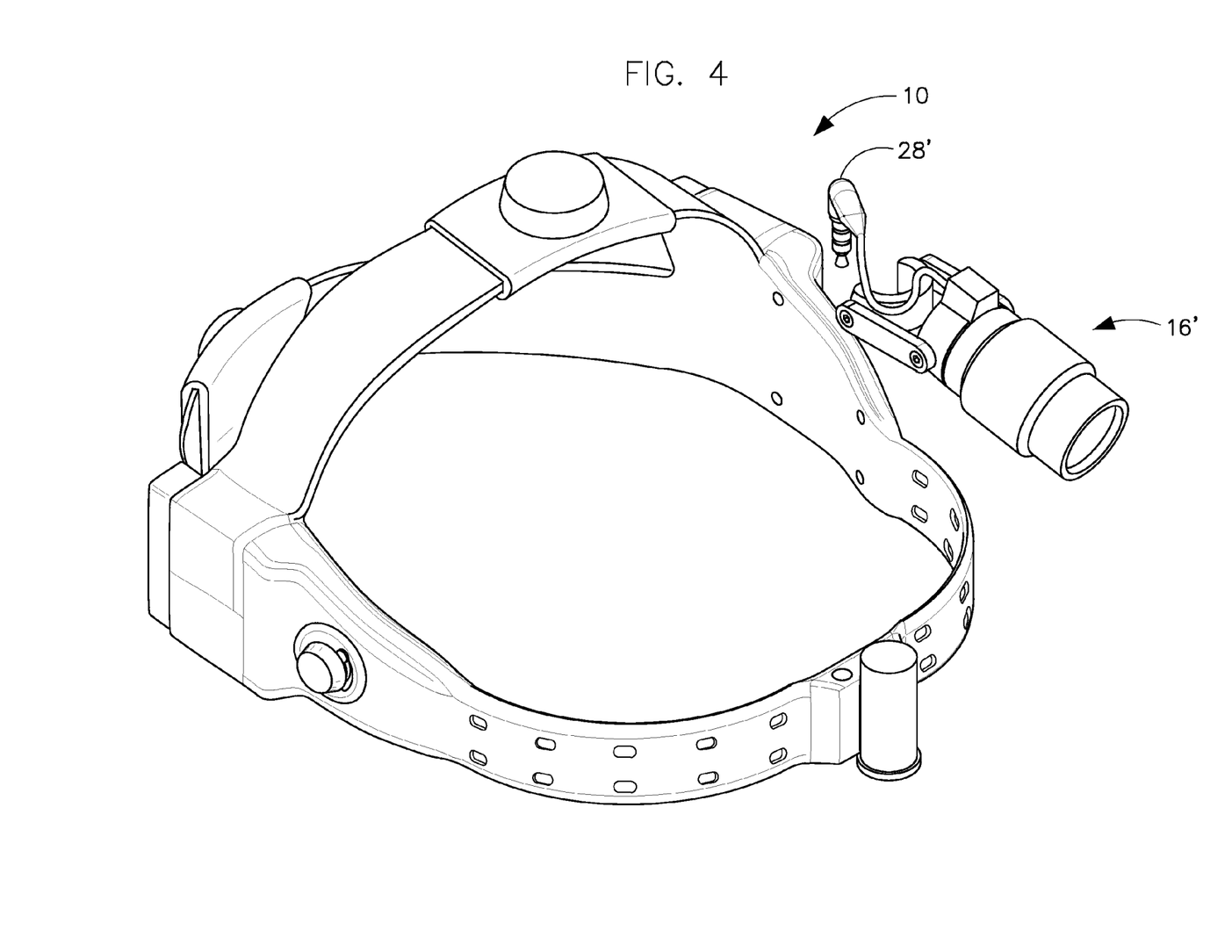
FIG. 4 shows an isometric view of a medical headlamp assembly, having a detached medical headlamp of the second type.
Figure 5:
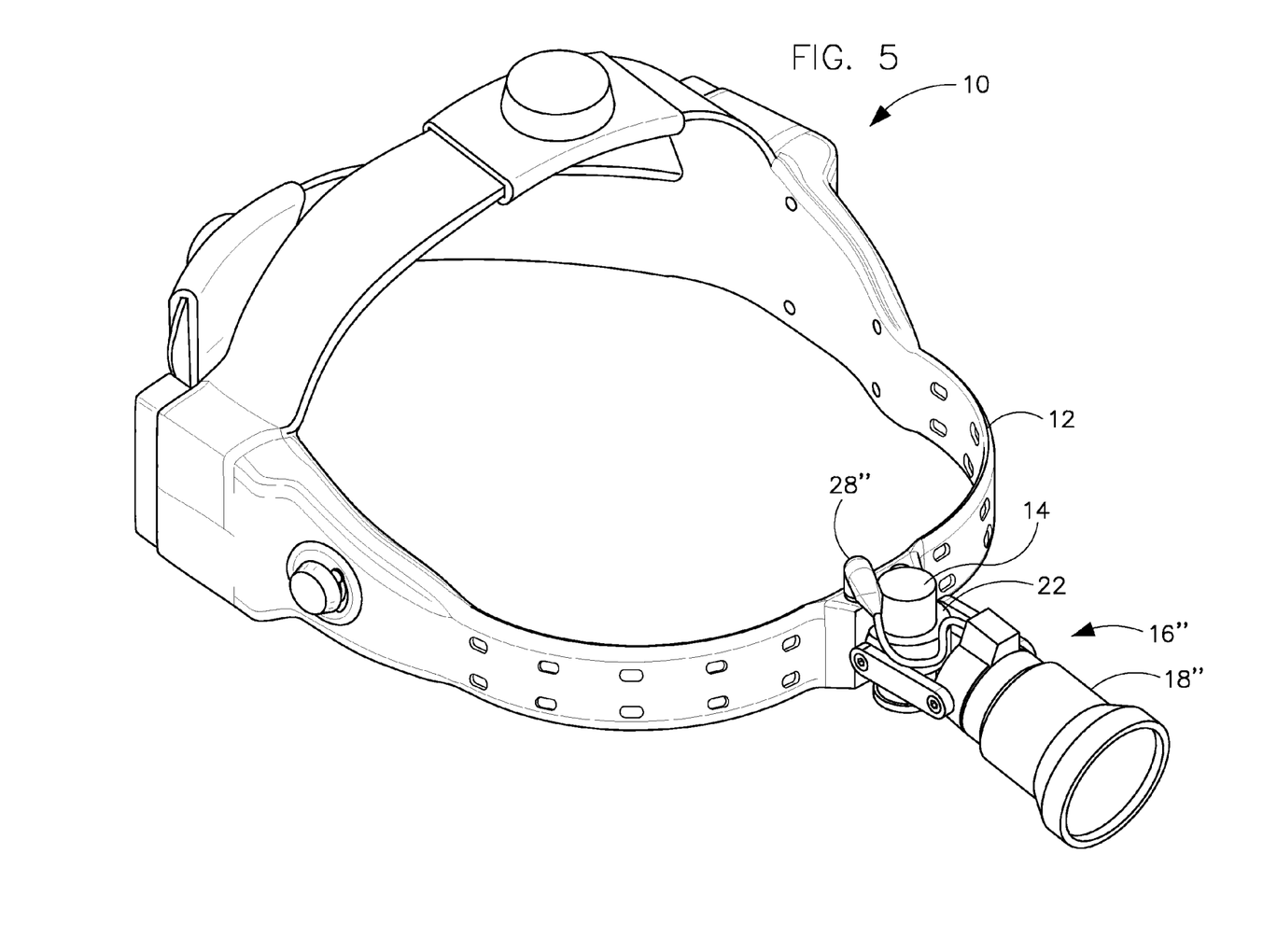
FIG. 5 shows an isometric view of a medical headlamp assembly, having an attached medical headlamp of a third type.
Figure 6:
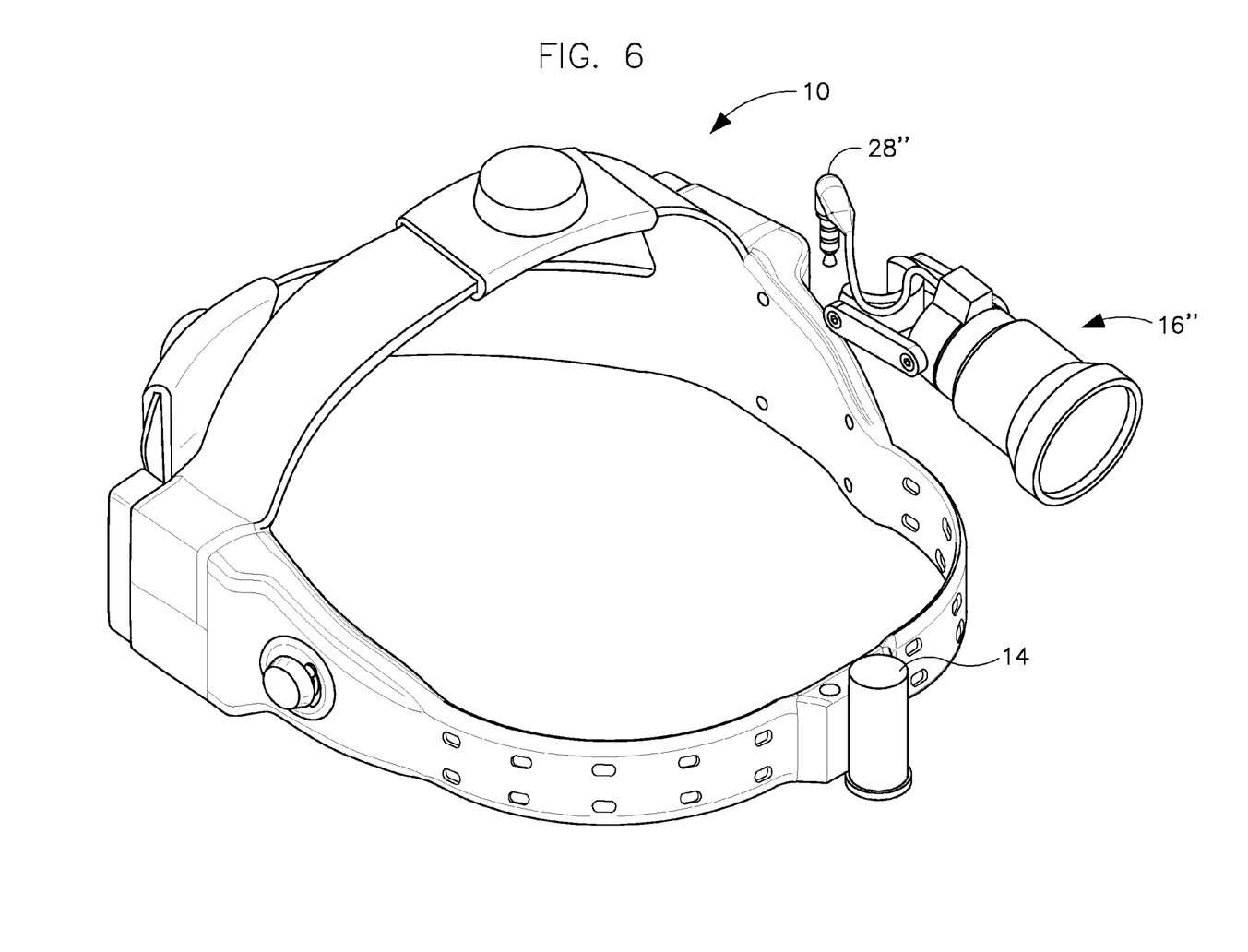
FIG. 6 shows an isometric view of a medical headlamp assembly, having a detached medical headlamp of the third type.

As shown in FIG. 2, when a user decides that he would like to remove assembly 16 from mounting column 14, he pulls assembly 16 upwardly to disengage slider 22 from column 14 and unplugs plug 28 from jack 30. He may do this simply to replace a worn out assembly 16, or (referring to FIG. 3) to install an assembly having different characteristics, such as medium intensity assembly 16', having medium intensity light 18' and plug 28' which is plugged into jack 30. Referring to FIGS. 5 and 6, in like manner assembly 16' can be switched out and assembly 16", having high intensity light 18" and plug 28", can be installed onto slider 22 on column 14, and with plug 28" plugged into jack 30.

Figure 7:
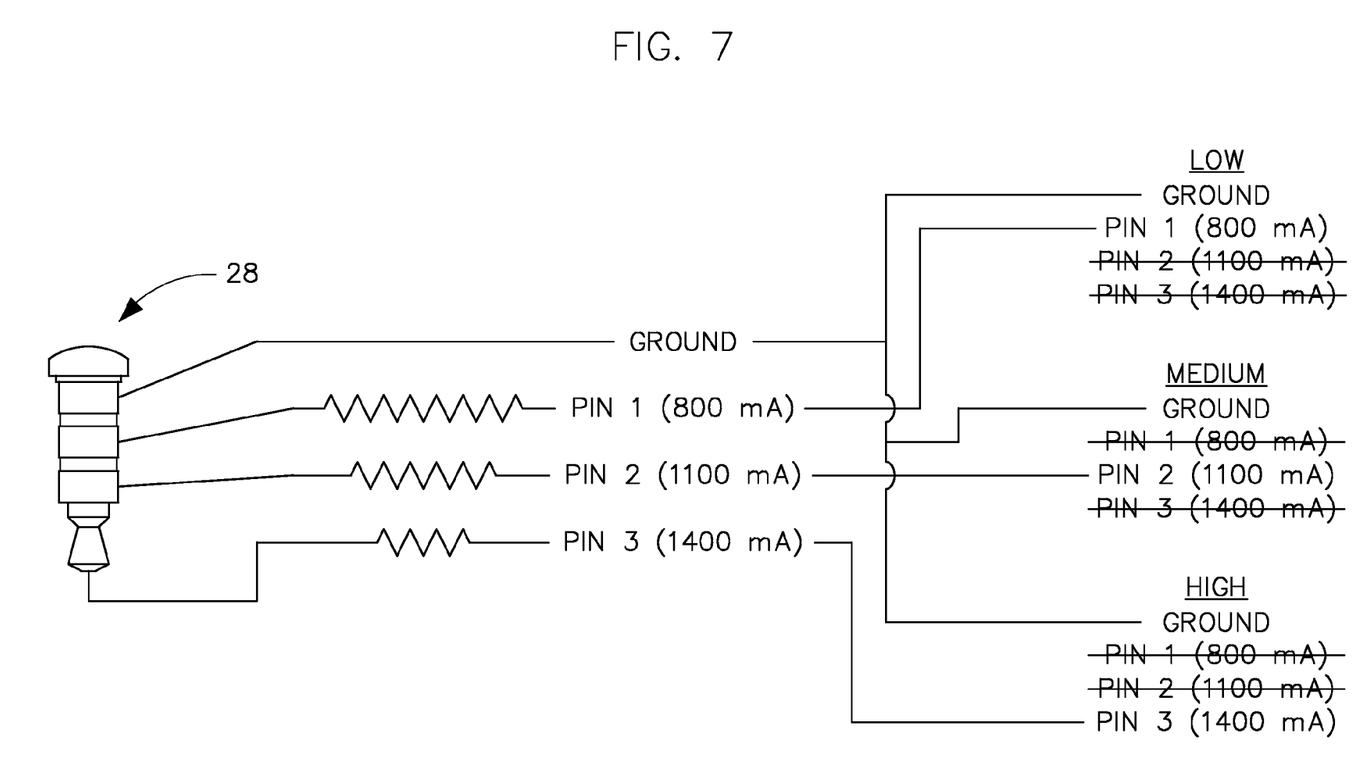
FIG. 7 shows an audio plug and the scheme of use of the poles of the audio plug that is used in a preferred embodiment of the present invention.

Referring to FIG. 7, although plugs 28, 28' and 28" appear identical, each one has a different active pin (longitudinally arranged electrical contact) that is electrically connected to the light emitting diode (not shown) of lamp 18, 18' or 18", respectively, and serving as the return, with the current being delivered into lamp 18, 18' and 18" in all cases through the ground. Pin 1 of plug 28 serves as the LED return for lamp 18, pin 2 serves as the LED return for lamp 18', and pin 3 serves as the LED return for lamp 18". Pin 1, pin 2, and pin 3 of plug 28 connects to pin 2, pin 3 and pin 4 of jack 30, respectively. Pin 1 of jack 30 connects to the ground of plug 28.

Figure 8:
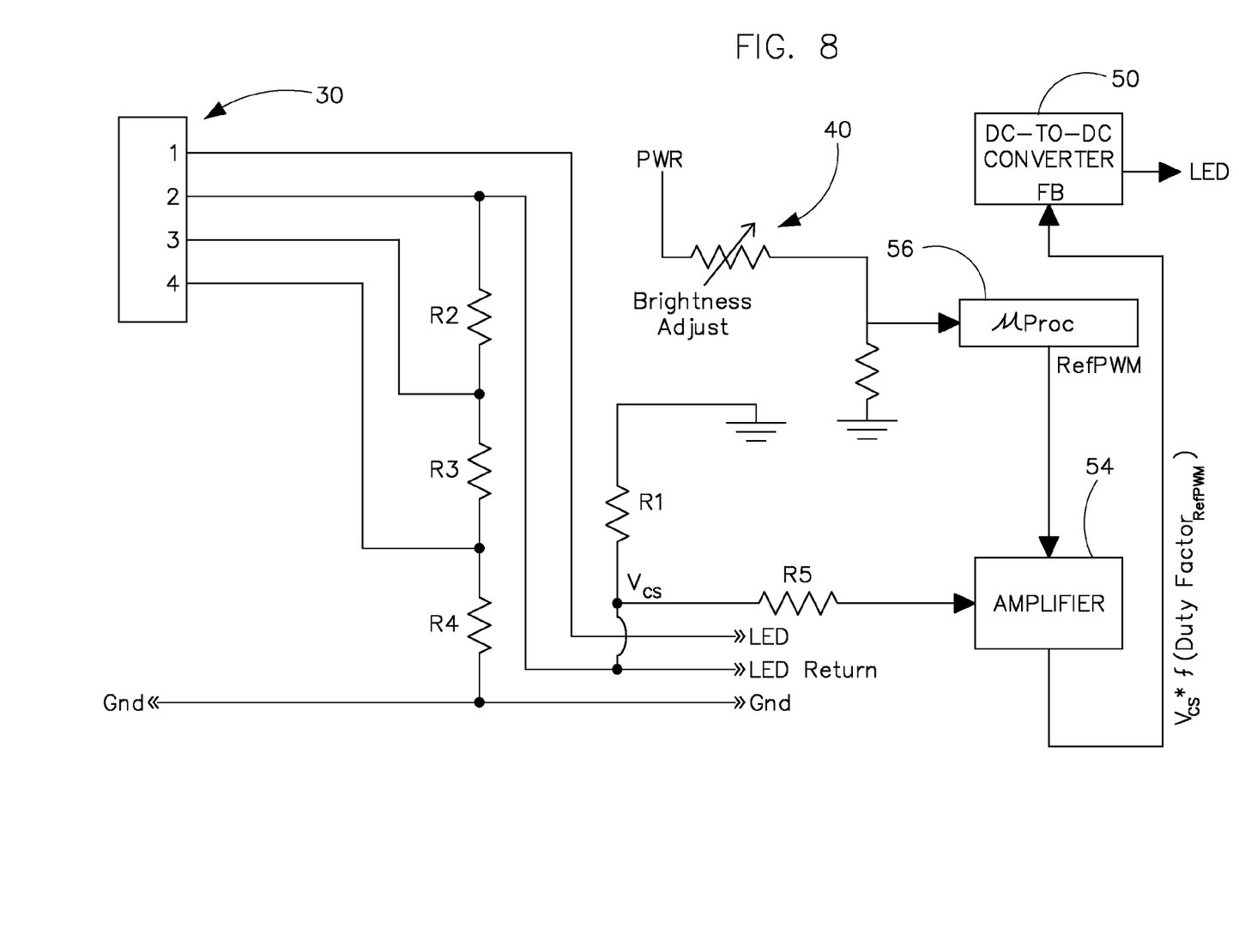
FIG. 8 shows a simplified schematic of the electrical network of the medical headlamp assembly of FIGS. 1-6.

Referring to FIG. 8, a DC-to-DC converter 50 acts as a power supply to whichever one of lamps 18, 18' or 18" is connected to jack 30. A feedback loop is formed by the output of converter 50 powering the LED line, where all of the current in which flows to the LED return line, and at least a portion of which passes through a current sense resistor R1, which in turn drives the feedback pin FB of converter 50. (The modification of the voltage at feedback pin FB through a voltage increase circuit 54 is described below.) The output of converter 50 increases if the voltage of feedback pin FB is below 0.5 volts and decreases if the voltage of feedback pin FB is above 0.5 volts, thereby setting that voltage at pin FB at 0.5 volts. Accordingly, when the voltage increase circuit 54 is not active, the voltage across resistor R1 is set at 0.5 volts, and accordingly, $I_{R1}$=R1/0.5 VDC. For the 800 mAmp lamp, for which the return current exits at Pin 2 of the jack 30, a few equations apply:

$$I_{R1} = 800 \text{ mAmps} - I_{R2}. \quad \text{Equation 1}$$

$$I_{R1} = \frac{800 \text{ mAmps} * (R_2 + R_3 + R_4)}{R_1 * (R_2 + R_3 + R_4 + 1)}. \quad \text{Equation 2}$$

For the 1.1 Amp lamp (from jack 30 pin 3) these equations become:

$$I_{R2,R1} = 1.1 \text{ mAmps} - I_{R3,R4}. \quad \text{Equation 1}_{1.1}$$

$$I_{R2,R1} = \frac{1.1 \text{ mAmps} * (R_3 + R_4)}{(R_1 + R_2) * (R_3 + R_4 + 1)}. \quad \text{Equation 2}_{1.1}$$

For the 1.4 Amp lamp (from jack 30 pin 4) these equations become:

$$I_{R3,R2,R1} = 1.4 \text{ mAmps} - I_{R4}. \quad \text{Equation 1}_{1.4}$$

$$I_{R3,R2,R1} = \frac{1.4 \text{ mAmps} * (R_4)}{(R_1 + R_2 + R_3) * (R_4 + 1)}. \quad \text{Equation 2}_{1.4}$$

In addition, for no lamp 18, 18', or 18" may the voltage drop through the lamp or the resistive network composed of $R_1$, $R_2$, $R_3$ and $R_4$ exceed a maximum that in one embodiment is about 3.4 volts. In addition, the power consumption of this resistive network must be minimized for all the lamps, leading to low values for all of the resistors, on the order of a little more than an ohm.

The voltage output of the brightness adjust rheostat 40 is fed into a pin of a microprocessor 56, resulting in a periodic waveform having a duty factor that is related to the rheostat output voltage, appearing on an output pin of the microprocessor 56. When the rheostat 40 is moved to a "dim" setting, this causes microprocessor 56 to produce a waveform that causes voltage increase circuitry 54 to amplify the voltage at its input, thereby reducing the current (and voltage) out of the DC-to-DC converter 50, and reducing the current through resistor R5. In an alternative preferred embodiment voltage increase circuitry is set to always amplify its input signal, thereby permitting a lower value for the voltage drop across $R_1$, when the lamp 18, 18' or 18" is not being dimmed. This permits a lower value of resistance for $R_1$, and lower power loss through $R_1$ and through the entire resistance network $R_1$, $R_2$, $R_3$ and $R_4$. For dimming positions of rheostat 40, this amplification is increased.

When the brightness adjust knob 40 is set at its maximum, causing a voltage increase circuit 54 (described below) to pass the voltage from a current sense resistor R1, unchanged, then the voltage through the current sense resistor R1 is forced to 0.5 volts by the feedback loop implemented by the converter 50 feedback pin FB (driven directly or indirectly by the current sense resistor R1, and the converter 50 output powering the lamp 18, 18' or 18", with the LED return line powering resistor R1).

Figure 9:
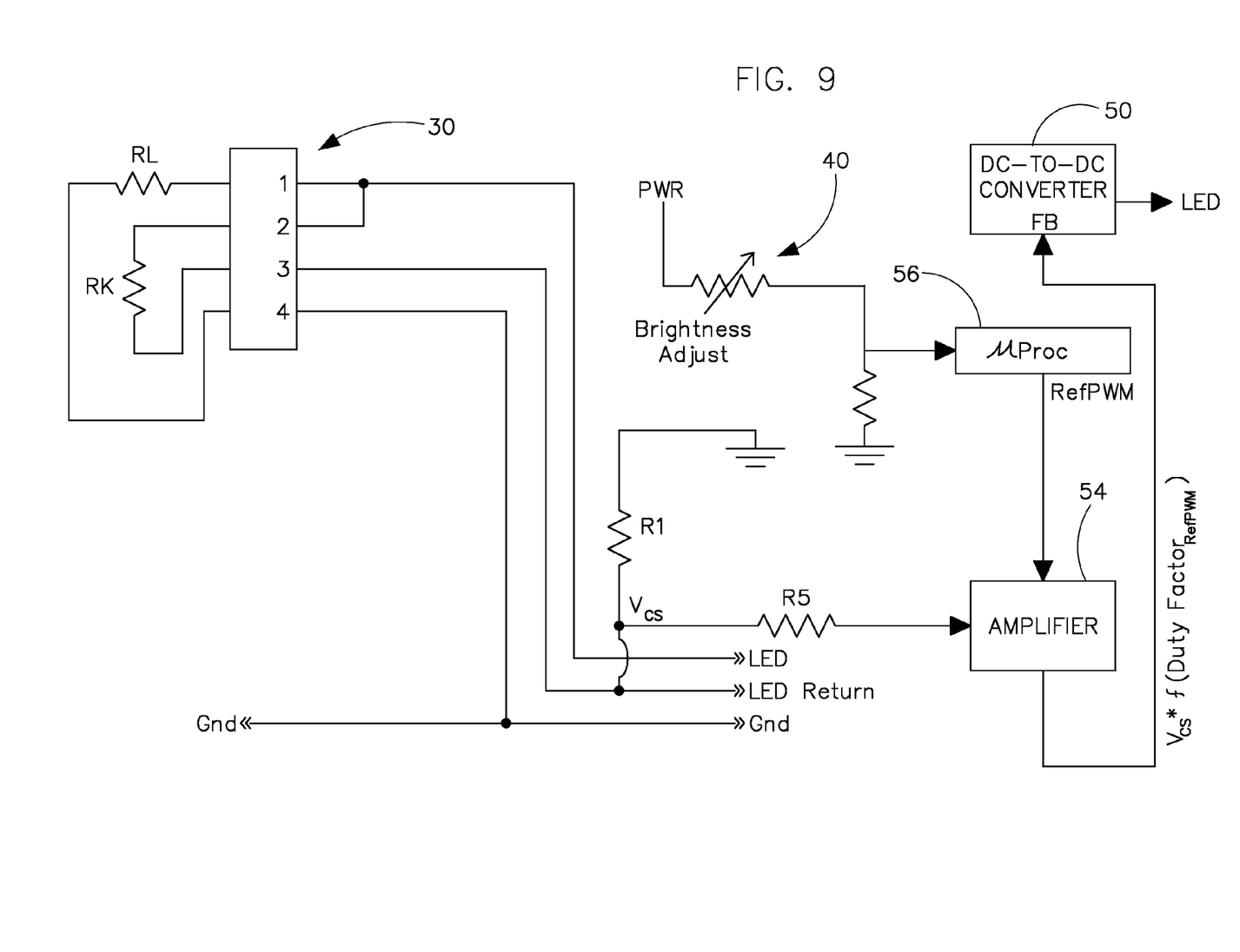
FIG. 9 shows a simplified schematic diagram of an alternative preferred electrical network of the of the medical headlamp assembly of FIGS. 1-6.

Referring to FIG. 9, in an alternative embodiment two of the pins of jack 30 are dedicated to connecting a key resistor $R_K$, which together with $R_1$ forms a voltage divider that determines the voltage $V_{CS}$, which drives amplifier 54, that drives the feedback input of the DC-to-DC Converter 50, which powers lamp 18, 18', or 18", having resistance value $R_L$, depending on which is being utilized. When, as noted above in reference to FIG. 8, microprocessor 56 is causing amplifier 54 to simply pass through $V_{CS}$ with unit gain to the feedback pin FB of convertor 50, then, for a specified $I_L$:

$$I_L * R_L * R_1 / (R_K + R_1) = 0.5 \text{ Volts; or}$$

$$I_L * R_L / 0.5 = (R_K + R_1) / R_1; \text{ or}$$

$$2 * I_L * R_L = R_K / R_1 + 1;$$

$$R_K = (2 * I_L * R_L - 1) * R_1$$

Accordingly, if the designer were to set $R_1$ to $5*10^5$ Ω to draw little current and save energy, $R_K$ would be set to $5*10^5*(1.6R_L-1)$, to set the correct voltage at the lamp 18 input to drive 800 mAmps through lamp 18. For 18', requiring 1.1 Amps, $R_K$ would be set at $5*10^5*(2.2R_L-1)$, (where $R_L$ would reflect the load of lamp 18', and would be somewhat different than the $R_L$ for 18). Finally, for lamp 18", $R_K$ equals $5*10^5*(2.8R_L-1)$.

Figure 10:
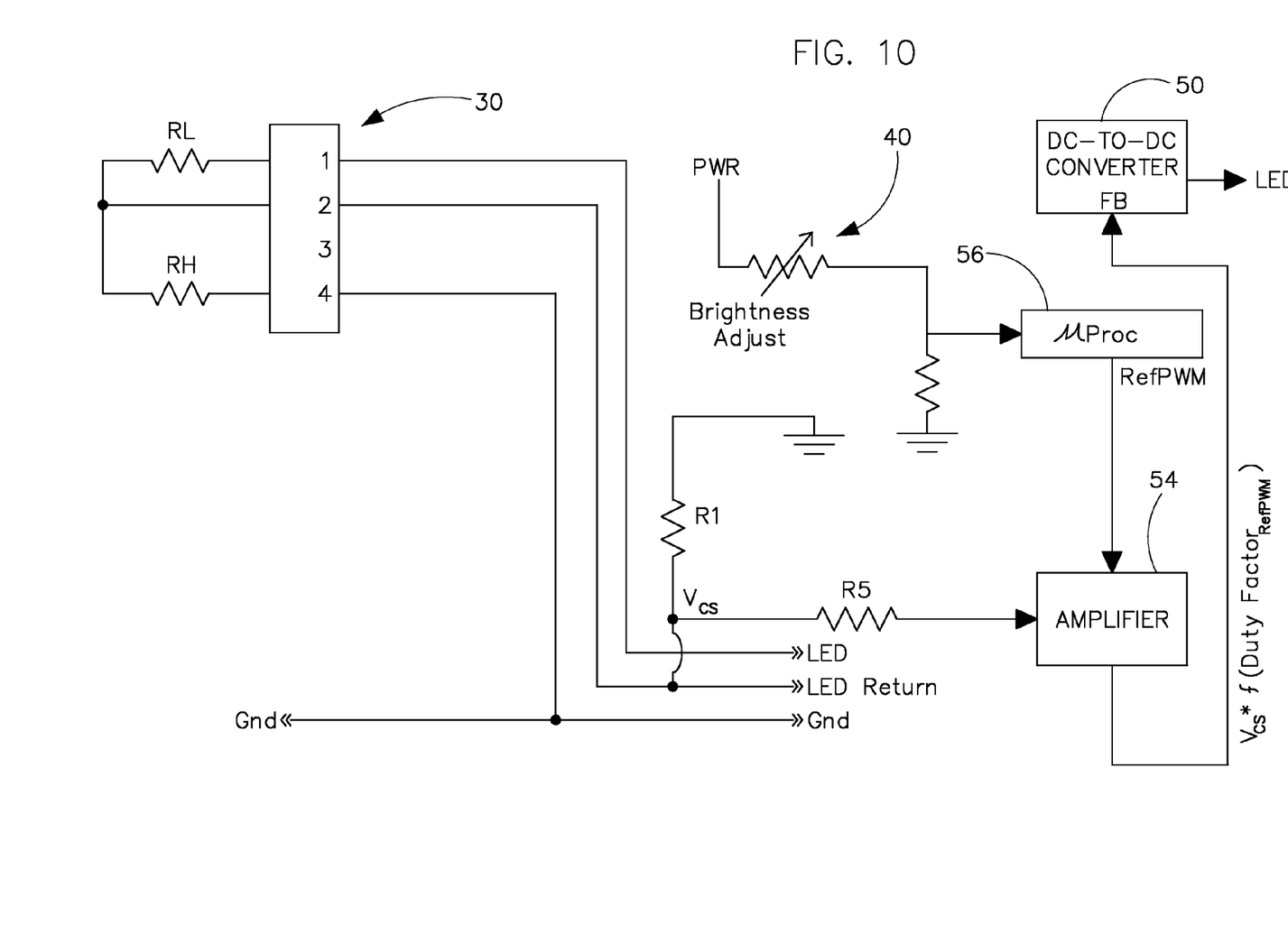
FIG. 10 shows a simplified schematic diagram of an additional alternative preferred electrical network of the of the medical headlamp assembly of FIGS. 1-6.

Now referring to FIG. 10, which sets the current through $R_L$, if $R_L$ is known precisely, then FIG. 9 and FIG. 10 will deliver the exact same current to $R_L$. But if $R_L$ differs slightly from an expected value, then the $V_L^2/R_L$ power achieved by fixing the voltage to a specified level that will be achieved by the FIG. 9 electrical network, will differ somewhat from the $I_L^2 * R_L$ power achieved by fixing current to a specified level, that will be achieved by the FIG. 10 electrical network. In general, for the FIG. 10 network:

$$R_K = R_1 / (2 * I_L - 1);$$

where $I_L$ is the specified value of current through the lamp.

For lamp 18, drawing 800 mAmps, $R_K=(5/3)*R_1$; for lamp 18', drawing 1.1 Amps, $R_K=(5/6)*R_1$; and for lamp 18", drawing 1.4 Amps, $R_K=(5/9)*R_1$.

In the embodiment of FIG. 9 it is power efficient to set $R_1$ and $R_K$ to high values resistance, whereas in the embodiment of FIG. 10, it is efficient to set them to low values of resistance.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A medical headlamp assembly, having:
   (a) a headband subassembly, including an electrical network, including a battery and an electrical jack, and a headlamp mount;
   (b) an electrical headlamp subassembly, having a mounting element matingly and removably engaged to said headlamp mount, and an electrical plug, matingly and removably engaged to said jack and an electrical headlamp, electrically connected to said plug; and
   (c) wherein said headband subassembly produces an electrical input for said headlamp subassembly and said headband subassembly includes a key resistor, the resistance value of which sets a characteristic of said electrical input.

2. The medical headlamp assembly of claim 1, wherein said electrical headlamp subassembly is a first electrical headlamp subassembly having a first key resistor and further including a second electrical headlamp subassembly, having a mounting element capable of removably mating to said headlamp mount and an electrical plug capable of removably mating to said jack and an electrical headlamp, electrically connected to said plug, and further including a second key resistor, having a different value from said first key resistor and which determines said electrical input at a different level than for said first headlamp subassembly.

3. The medical headlamp assembly of claim 1, wherein said resistance of said key resistor determines the voltage of said electrical input.

4. The medical headlamp assembly of claim 1, wherein said resistance of said key resistor determines the current value of said electrical input.

5. A method of switching out a medical headlamp, comprising:
   (a) providing a medical headlamp assembly having;
      (i) a headband assembly, including a mounting element, an electrical jack and a power supply assembly electrically connected to said electrical jack;
      (ii) a first headlamp assembly removably engaged to said mounting element and including a conductor terminating in a plug that is plugged into said jack, and a first key resistor for setting an electrical input; and
      (iii) a second headlamp assembly removeably engageable to said mounting element and including a conductor terminating in a plug that is engageable to said jack and a second key resistor for setting said electrical input differently than for said first headlamp;
   (b) removing said first headlamp assembly from said mounting element and unplugging said first headlamp plug from said jack; and
   (c) mounting said second headlamp on said mounting element and plugging said second headlamp plug into said jack.

6. The method of claim 5, wherein said second headlamp has different illumination characteristics from said first headlamp.

7. The medical headlamp assembly of claim 5, wherein said resistance of said first key resistor and said second key resistor each determine the voltage of said electrical input.

8. The medical headlamp assembly of claim 5, wherein said resistance of said first key resistor and said second key resistor, each determine the current value of said electrical input.

* * * * *

UNITED STATES PATENT AND TRADEMARK OFFICE
CERTIFICATE OF CORRECTION

| | | |
|---|---|---|
| PATENT NO. | : 9,568,177 B2 | Page 1 of 1 |
| APPLICATION NO. | : 14/750754 | |
| DATED | : February 14, 2017 | |
| INVENTOR(S) | : John Thomas Ferguson | |

It is certified that error appears in the above-identified patent and that said Letters Patent is hereby corrected as shown below:

On the Title Page

In the Abstract:
In Lines 12-16, the second occurrence of the word "headband" in Line 14 should be replaced with the word "headlamp".

In the Specification

In the Summary:
In the first full paragraph, Lines 14-18, the second occurrence of the word "headband" in Line 16 should be replaced with the word "headlamp".

In the Claims

In Lines 14-19, in Claim 1, paragraph (c), the second occurrence of the word "headband" in Line 16 should be replaced with the word "headlamp".

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*